United States Patent [19]

Levine et al.

[11] Patent Number: 5,344,822
[45] Date of Patent: Sep. 6, 1994

[54] METHODS USEFUL IN ENDOTOXIN PROPHYLAXIS AND THERAPY

[75] Inventors: Daniel M. Levine, New York; Thomas S. Parker, Brooklyn, both of N.Y.; Albert L. Rubin, Englewood, N.J.

[73] Assignee: The Rogosin Institute, New York, N.Y.

[21] Appl. No.: 928,930

[22] Filed: Aug. 12, 1992

[51] Int. Cl.⁵ .......................... A61K 37/02; C07K 7/08
[52] U.S. Cl. .......................... 514/13; 514/2; 514/12
[58] Field of Search ................. 514/2, 12, 13

[56] References Cited

U.S. PATENT DOCUMENTS 5,128,318  7/1992  Levine .

OTHER PUBLICATIONS

Anantharamiah, "Methods in Enzymology", vol. 128, pp. 627–647 (1986).

*Primary Examiner*—Lester L. Lee
*Attorney, Agent, or Firm*—Felfe & Lynch

[57] ABSTRACT

Treatment and prophylaxis of endotoxin caused toxicity is disclosed. This is accomplished by administering a lipid into which the endotoxin of concern is associated, preferably together with a peptide which is not an apolipoprotein. Preferably, the two components are administered in the form of a reconstituted particle, although this is by no means required.

7 Claims, 8 Drawing Sheets

Nonpolar Face

Polar Face
18A

Nonpolar Face

Polar Face
Reverse 18A

Polar Face
des Val¹⁰ 18A

Polar Face
AP

LAP-24

APOA-I CONSENSUS

APOA–IV CONSENSUS

METHODS USEFUL IN ENDOTOXIN PROPHYLAXIS AND THERAPY

FIELD OF INVENTION

This invention relates to the treatment of endotoxin poisoning. More particularly, it relates to the treatment of such poisoning via administration of various compositions which act to remove endotoxins from the organism.

BACKGROUND AND PRIOR ART

Normal serum contains a number of lipoprotein particles which are characterized according to their density, namely, chylomicrons, VLDL, LDL and HDL. They are composed of free and esterified cholesterol, triglycerides, phospholipids, several other minor lipid components, and protein. Low density lipoprotein (LDL) transports lipid soluble materials to the cells in the body, while high density lipoprotein (HDL) transports these materials to the liver for elimination. Normally, these lipoproteins are in balance, ensuring proper delivery and removal of lipid soluble materials. Abnormally low HDL can cause a number of diseased states as well as constitute a secondary complication in others.

Under normal conditions, a natural HDL particle is a solid with its surface covered by a phospholipid bilayer that encloses a hydrophobic core. Apolipoprotein A-I and A-II attach to the surface by interaction of the hydrophobic face of their alpha helical domains. In its nascent or newly secreted form the particle is disk-shaped and accepts free cholesterol into its bilayer. Cholesterol is esterified by the action of lecithin:cholesterol acyltransferase (LCAT) and is moved into the center of the disk. The movement of cholesterol ester to the center is the result of space limitations within the bilayer. The HDL particle "inflates" to a spheroidal particle as more and more cholesterol is esterified and moved to the center. Cholesterol ester and other water insoluble lipids which collect in the "inflated core" of the HDL are then cleared by the liver.

Jonas et al., *Meth. Enzym.* 128A: 553–582 (1986) have produced a wide variety of reconstituted particles resembling HDL. The technique involves the isolation and dilapidation of HDL by standard methods (Hatch et al., *Adv. Lip. Res.* 6: 1–68 (1968); Scanu et al., *Anal. Biochem.* 44: 576–588 (1971) to obtain apo-HDL proteins. The apoproteins are fractionated and reconstituted with phospholipid and with or without cholesterol using detergent dialysis.

Matz et al., *J. Biol. Chem.* 257(8): 4535–4540 (1982) describe a micelle of phosphatidylcholine, with apolipoprotein A1. Various ratios of the two components are described, and it is suggested that the described method can be used to make other micelles. It is suggested as well to use the micelles as an enzyme substrate, or as a model for the HDL molecule. This paper does not, however discuss application of the micelles to cholesterol removal, nor does it give any suggestions as to diagnostic or therapeutic use.

Williams et al., *Biochem. & Biophys. Acta* 875: 183–194 (1986) teach phospholipid liposomes introduced to plasma which pick up apoproteins and cholesterol. Liposomes are disclosed, which pick up apoprotein in vivo, as well as cholesterol, and it is suggested that the uptake of cholesterol is enhanced in phospholipid liposomes which have interacted with, and picked up apoproteins.

Williams et al., *Persp. Biol. & Med.* 27(3): 417–431 1984) discuss lecithin liposomes as removing cholesterol. The paper summarizes earlier work showing that liposomes which contain apoproteins remove cholesterol form cells in vitro more effectively than liposomes which do not contain it. They do not discuss in vivo use of apoprotein containing liposomes or micelles, and counsel caution in any in vivo work with liposomes.

It is important to note that there is a clear and significant difference between the particles of the present invention, and the liposomes and micelles described in the prior art. The latter involve a bilayer structure of lipid-containing molecules, surrounding an internal space. The construction of liposomes and micelles precludes filling the internal space, however, and any molecular uptake is limited to the space defined between the two lipid layers. As a result, there is much less volume available for pick up and discharge of materials such as cholesterol and other lipid soluble materials than there is for the particles of this invention, which expand in a fashion similar to a balloon, with interior space filling with the material of choice.

Anantharamaiah, in Segrest et al., *Meth. Enzymol.* 128: 627–647 (1986) describe a series of peptides which form "helical wheels", as a result of the interaction of the amino acids in the peptide with each other. Such helical wheels present a nonpolar face, and a polar face in their configuration.

Endotoxic shock is a condition, often fatal, provoked by the outer membrane of most gram negative bacteria (e.g., *Escherichia coli; Salmonella typhimurium*). The structure of the bacterial outer membrane has been fairly well elucidated, and a unique molecule, referred to as lipid A, which is linked to acyl chains via lipid A molecule's glucosamine backbone. See Raetz, *Ann. Rev. Biochem.* 59: 129–170 (1990) in this regard.

The lipid A molecule serves as membrane anchor of a lipopolysaccharide structure ("LPS") and it is the LPS which is implicated in the development of endotoxic shock. It should be pointed out that LPS molecules are characterized by a lipid A type structure and a polysaccharide portion. This latter moiety may vary in molecular details in different LPS molecules, but it will retain the general structural motifs characteristic of endotoxins. It would be incorrect to say that the LPS molecule is the same from bacteria to bacteria (see Raetz, supra). It is common in the art to refer to the various LPS molecules as "endotoxins", and this term will be used hereafter to refer to LPS molecules collectively.

In U.S. Pat. No. 5,128,318 the disclosure of which is incorporated by reference, it was taught that reconstituted particles containing both an HDL associated apolipoprotein and a lipid capable of binding an endotoxin to inactivate it could be used as effective materials for alleviating endotoxin caused toxicity.

It has now been found that various other materials may be used to treat endotoxin caused toxicity. Specifically, it has been found that apolipoproteins are not required in reconstituted particles, and that the reconstituted particle may contain a peptide and a lipid as defined supra, wherein the peptide is not an apolipoprotein.

It has also been found that endotoxin caused toxicity may be treated via sequential administration of either an apolipoprotein or a peptide followed by a lipid as described supra. It appears that following sequential administration the components assemble as a reconstituted particle and then act to remove endotoxin.

It has also been found that at least some individuals possess native levels of apoliprotein which are higher than normal levels such that effective endotoxemia therapy may be effectuated by administering reconstituted particles containing no apolipoprotein or peptide, but containing the lipid described supra.

In addition, the invention involves the use of the reconstituted particles and the components discussed herein for prophylaxis against endotoxin caused toxicity, by administering prophylactically effective amounts to subjects in need of prophylaxis.

These and other aspects of the invention are described in the disclosure which follows.

DETAILED DESCRIPTION OF THE EMBODIMENTS

EXAMPLE 1

Studies were carried out to determine the survival rate of mice challenged with *S. typhimurium* endotoxin. Outbred male, Swiss-Webster mice received either saline (20 mice), reconstituted HDL particles (40 mice), or reconstituted peptide 18A (20 mice), via injection through the tail vein. The particulars of the injection materials are as follows:

a. HDL particles

Particles were prepared from apo-Hu--HDL (85%- AI; 15% AII and apo C), reconstituted with 95% pure egg phosphatidylcholine (2:1 W/W), using detergent dialysis, in accordance with Matz et al., J. Biol. Chem. 257: 4535-4540 (1982), and U.S. Pat. No. 5,128,318, the disclosure of which is incorporated by reference.

b. peptide particles

The peptide 18A has the amino acids sequence: Asp-Trp-Leu-Lys-Ala-Phe-Tyr-Asp-Lys-Val-Ala-Glu-Lys-Leu-Lys-Glu-Ala-Phe Samples of peptide were also mixed and reconstituted with 95% pure eggs phosphatidylcholine as per Matz et al., supra (2:1 W/W), and U.S. Pat. No. 5,128,318 also using detergent dialysis. The resulting particles are identical to those disclosed in U.S. Pat. No. 5,128,318 except that a peptide component was present, rather than the apo-HDL of the Matz and patent references.

Figure 3:
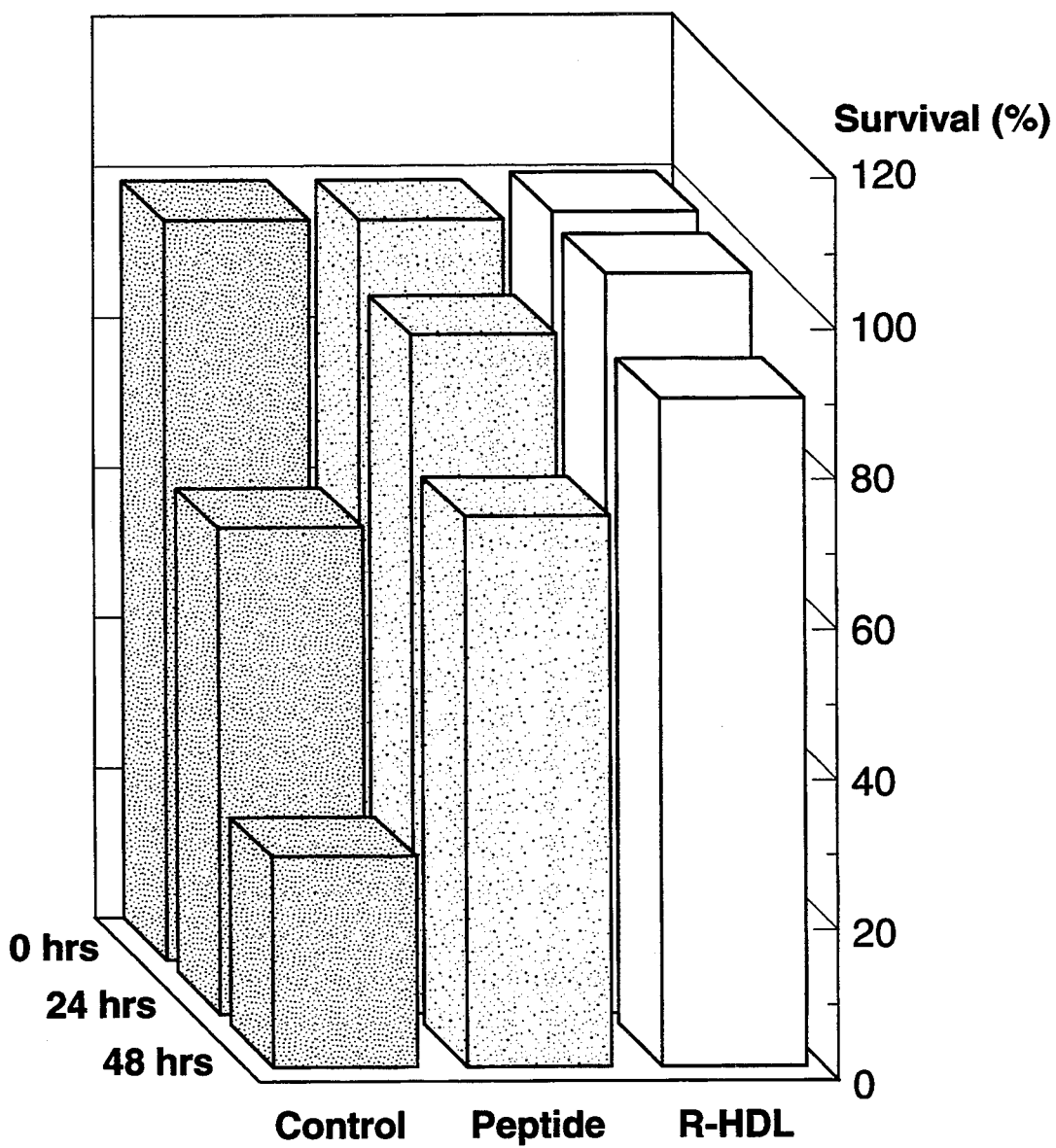
FIG. 3 shows experiments in which a peptide in accordance with the invention as used to study reduction of endotoxin caused toxicity in a mouse model.
Figure 4A:
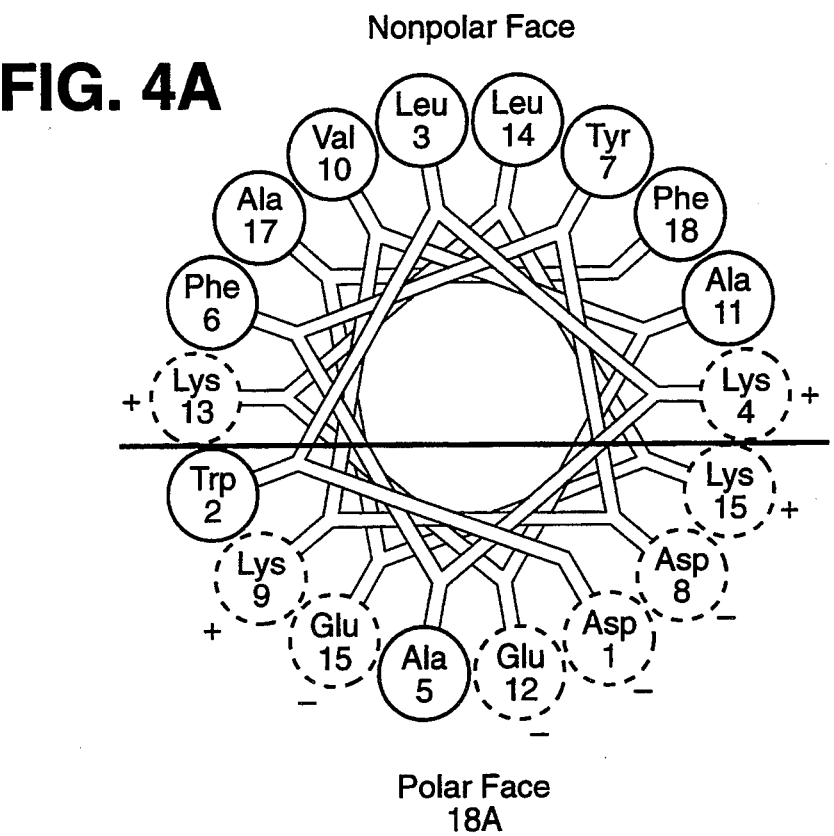
FIGS. 4A–4I, inclusive, each show a helical wheel formed by a peptide.
Figure 4B:
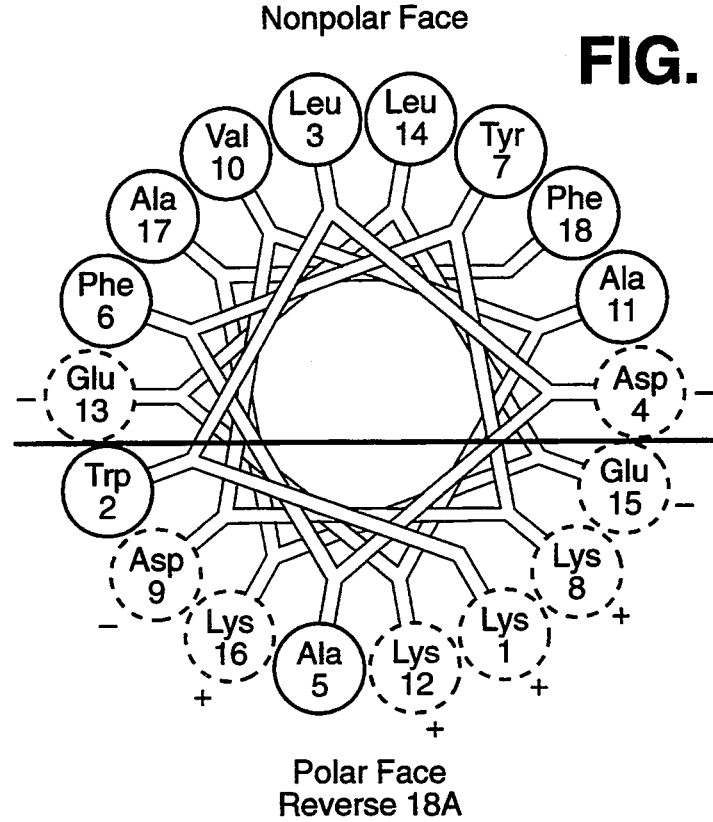
Figure 4C:
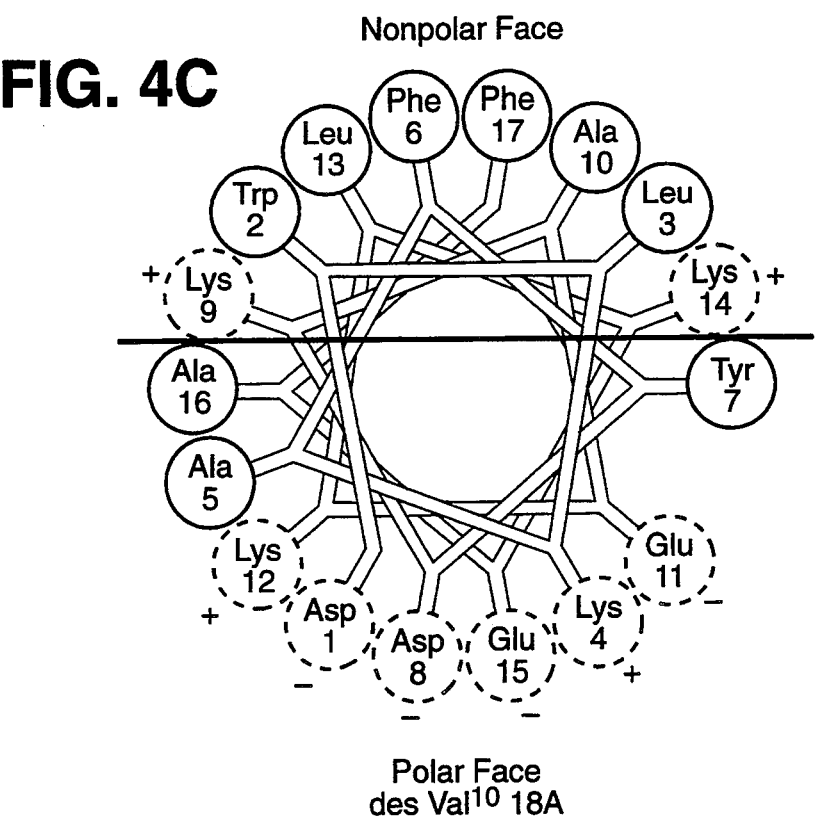
Figure 4D:
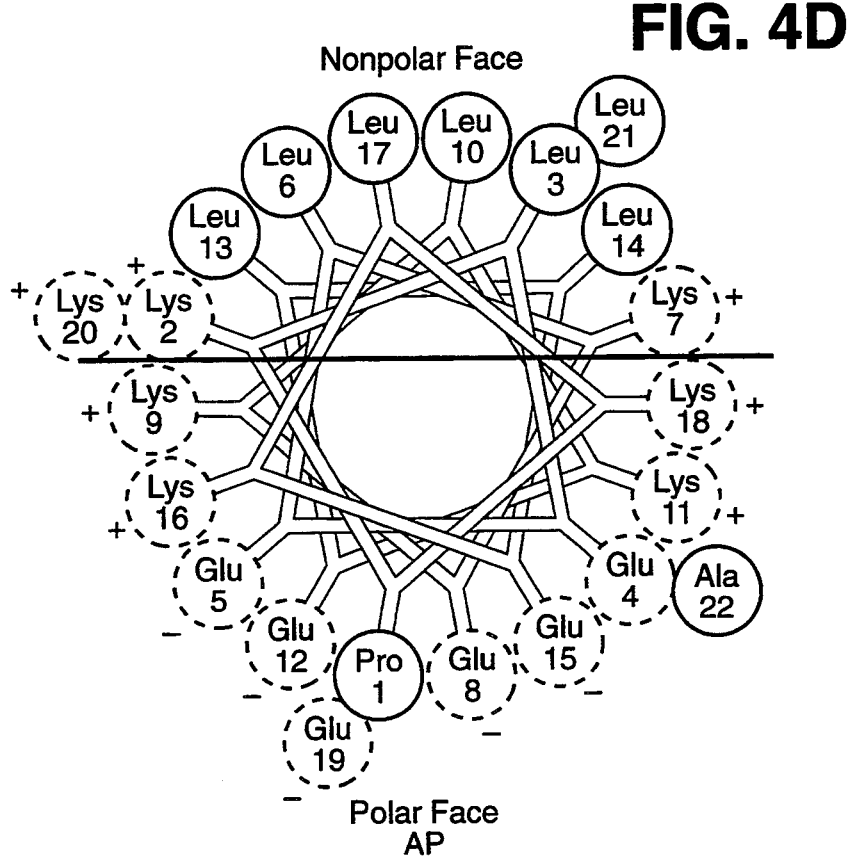
Figure 4E:
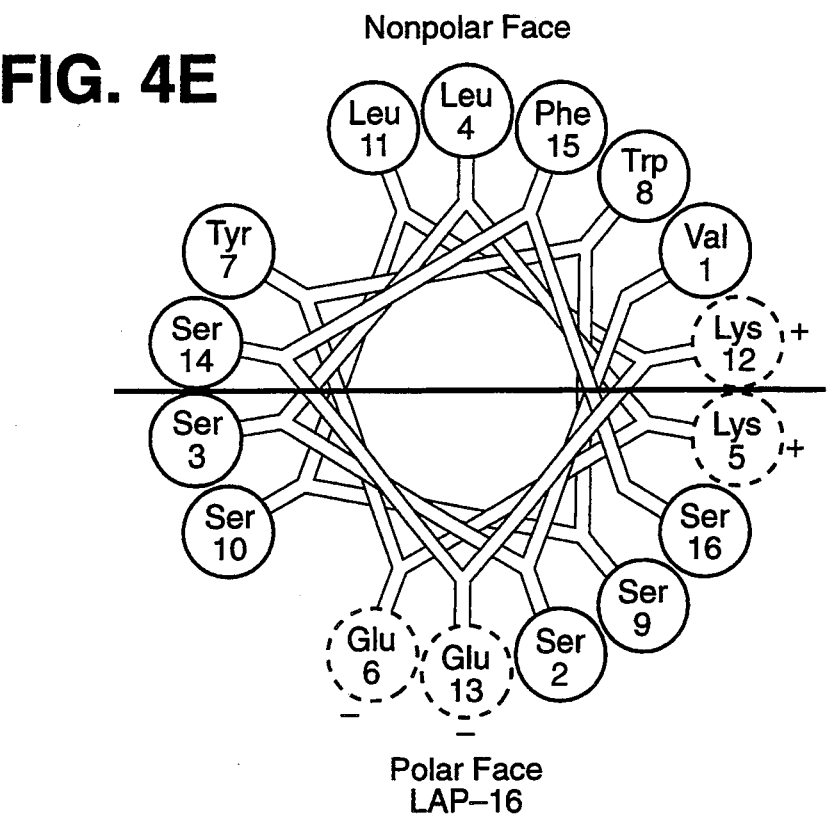
Figure 4F:
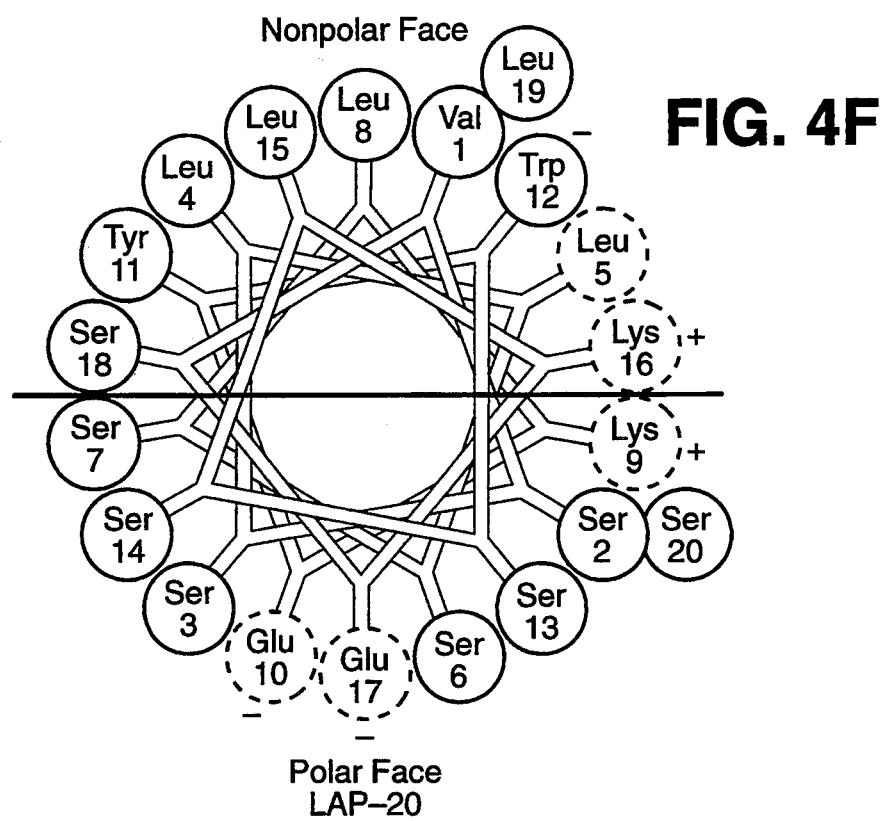
Figure 4G:
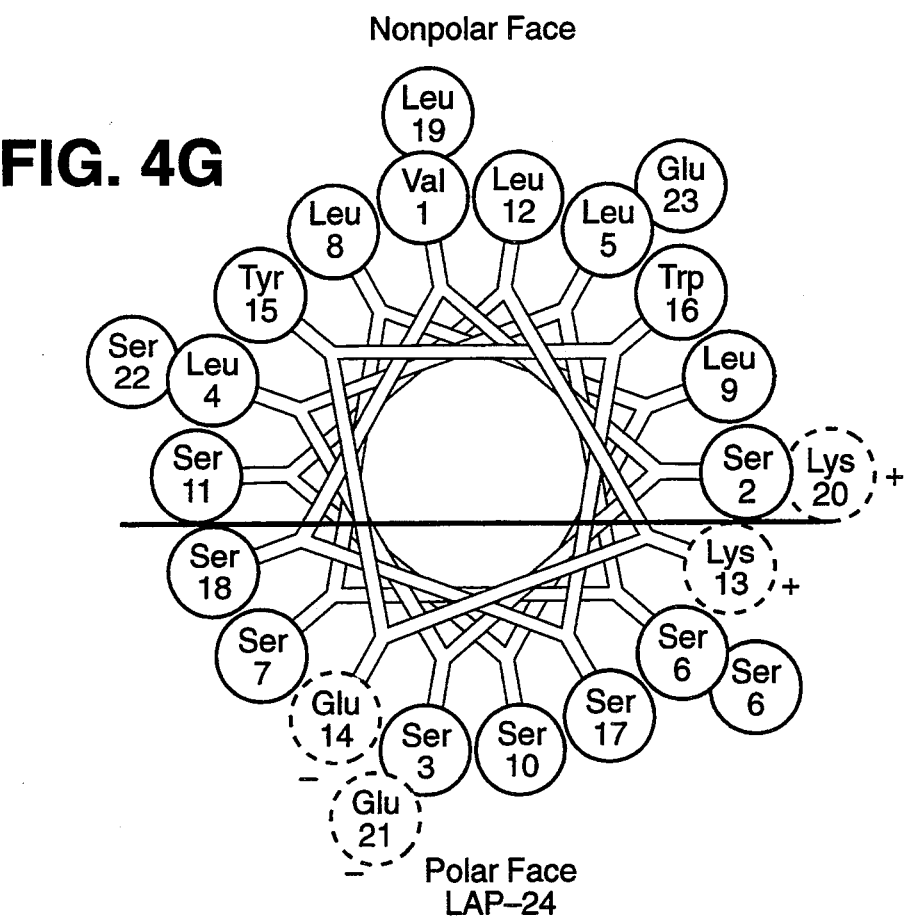
Figure 4H:
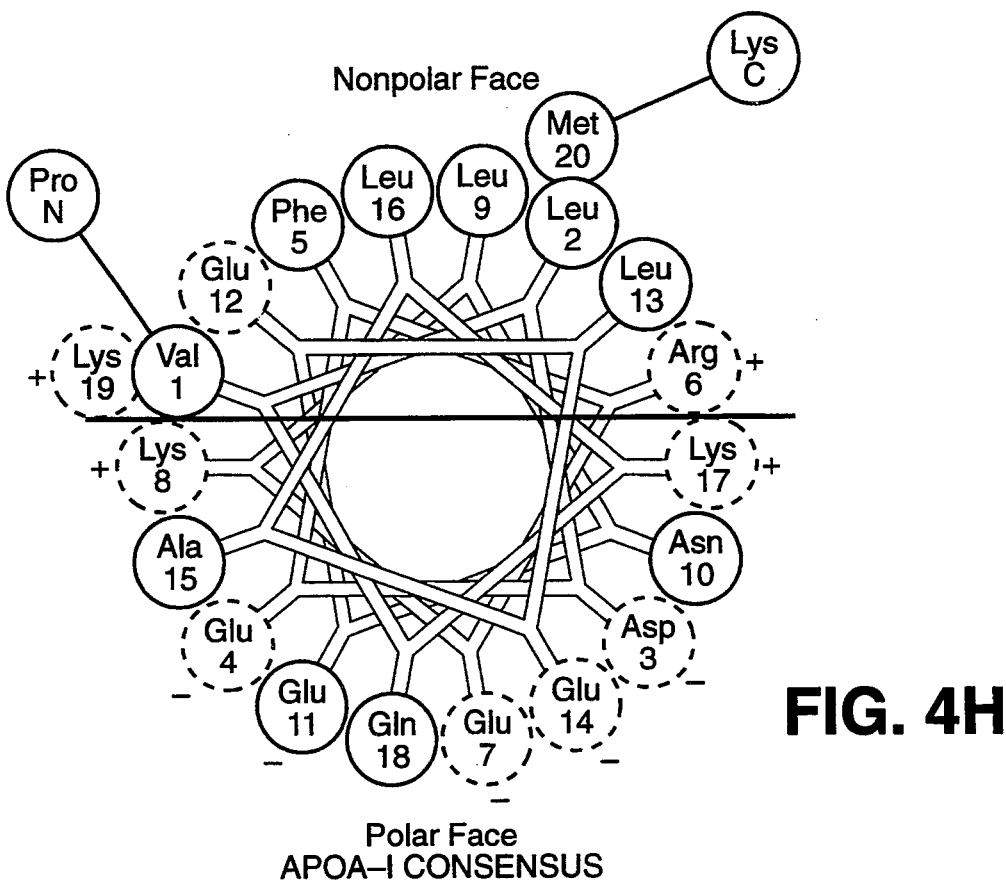
Figure 4I:
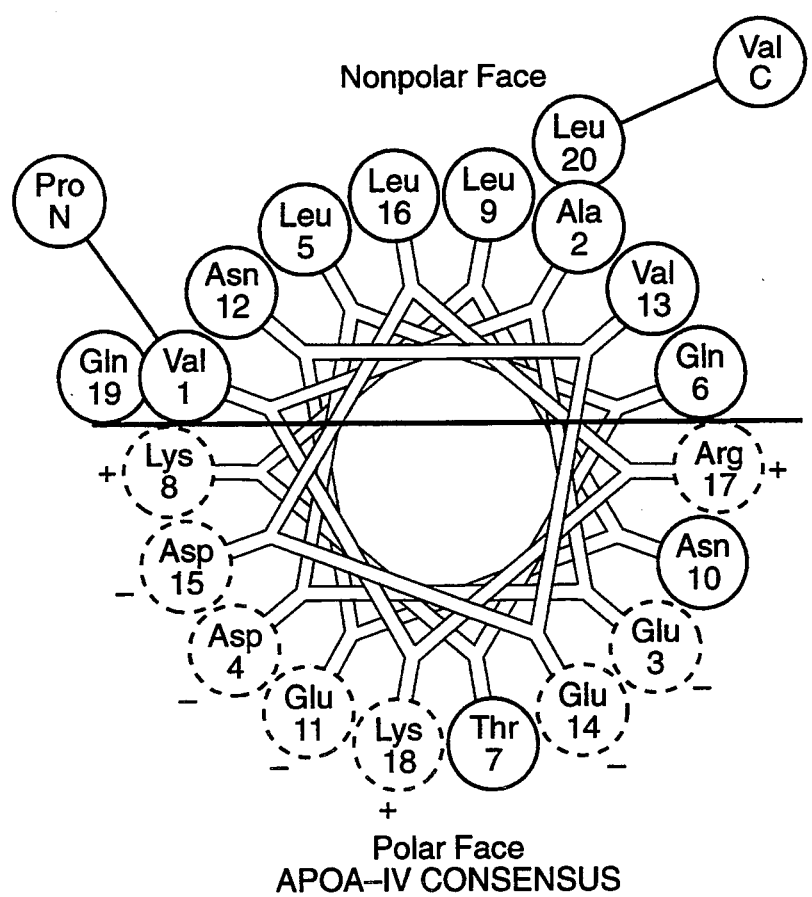

Within fifteen minutes of administration of the reconstituted material, the mice were administered, intraperitoneally, 10 mg/kg body weight of Salmonella LPS. The criterion for evaluation was survival. FIG. 3 presents these results, and indicates nearly 4 fold superiority over the saline control. The synthetic peptide is almost as effective as the reconstituted apo-HDL containing particles.

Figure 1:
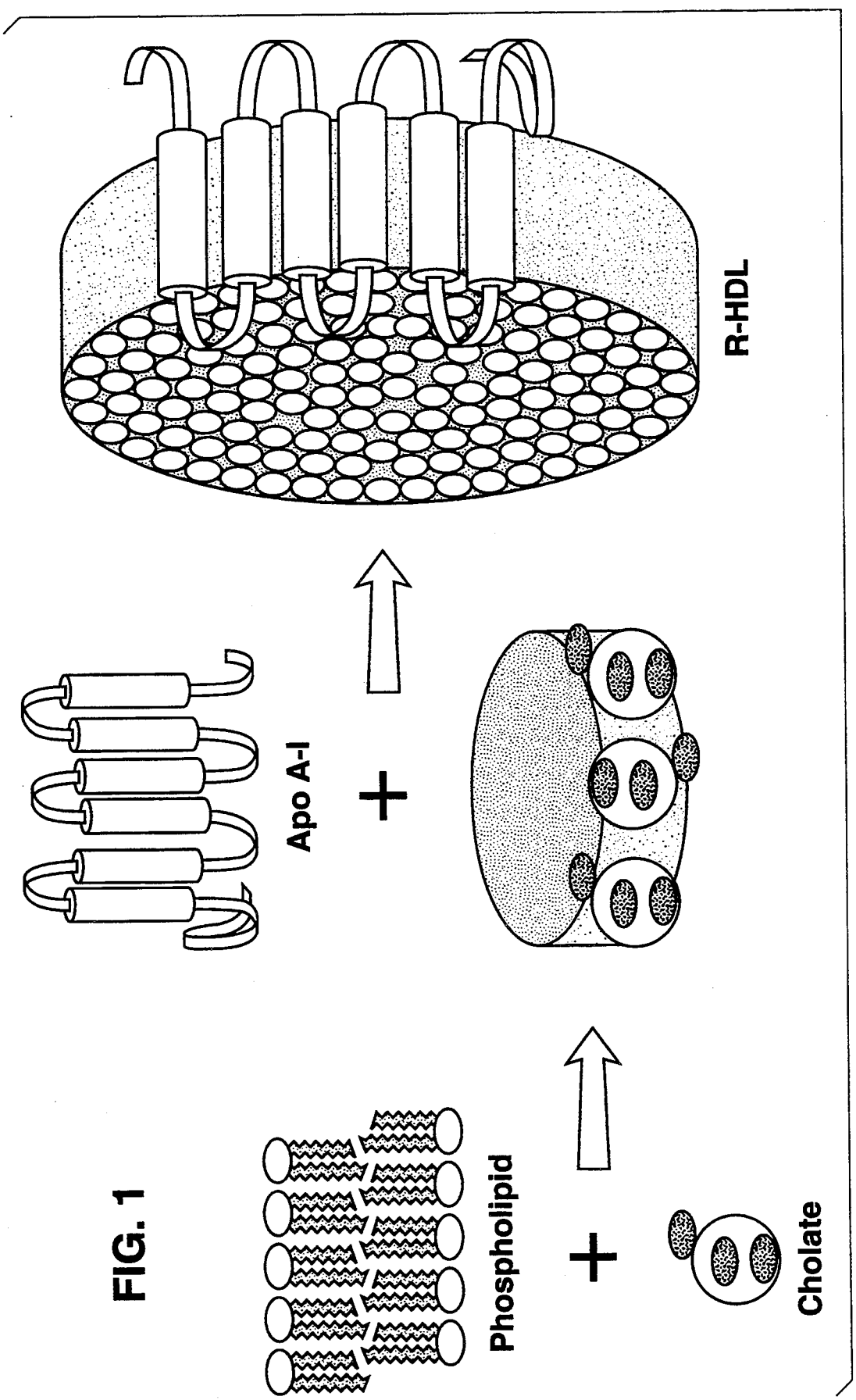
FIG. 1 shows how reconstituted particles containing Apo-A1, phospholipid and cholate form.
Figure 2:
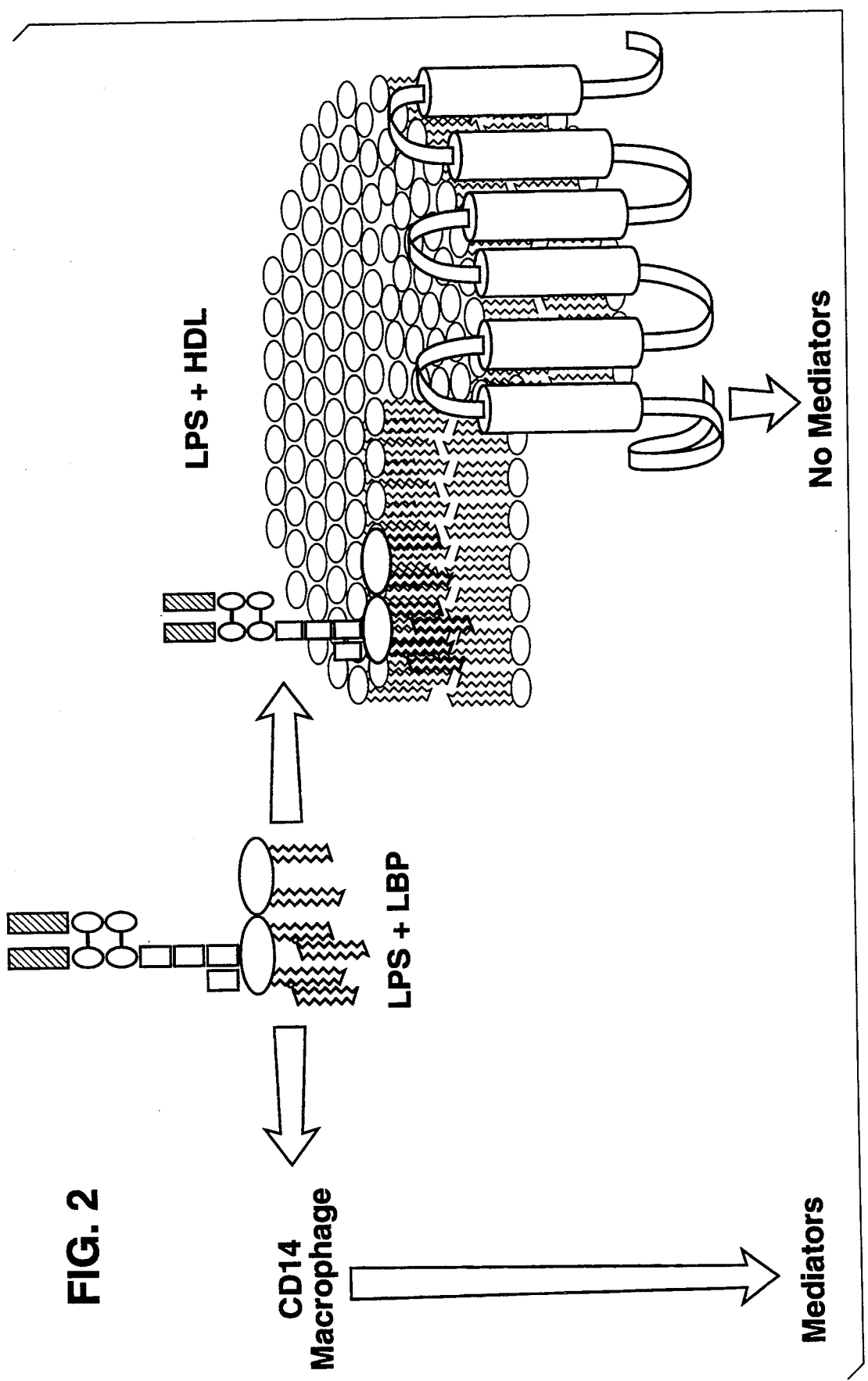
FIG. 2 shows the reception of LPS molecules by reconstituted particles.

The examples infra show the efficacy of various treatment methodologies for alleviating endotoxin caused toxicity. The feature which unites all forms of therapy described herein is the need for both a peptide or an apolipoprotein to be present, and a lipid in which the endotoxin causative agent associates. "Associates", as the term is used herein refers to the interaction of lipid and the lipid portion of the endotoxin molecule. The interaction permits removal of the endotoxin by the particle structure to a clearing site in the body, particularly the liver. FIG. 2 shows the mechanism of association.

The therapeutic efficacy attained with the invention described herein also suggests adaptation of the methodology for prophylaxis against endotoxemia. There are very well recognized situations where individuals are put at risk for exposure to endotoxins including, but not limited to surgery, treatment of wounds, and so forth. The invention encompasses prophylactic methodologies wherein an individual at risk for endotoxemia receives an effective amount of the described materials sufficient to prevent or to lower the risk of endotoxemia. The various situations in which an individual is exposed to endotoxins are well known to the skilled artisan and need not be repeated here.

The therapeutic regimen described supra involves the administration of reconstituted particles containing peptide and lipid. It is also possible to administer the components of the particles separately—i.e., individual doses of the peptide and the lipid, or one of each. The dosing may be sequential or simultaneous. It is also within the scope of the invention to treat some patients by administering only the lipid component or only the peptide component. Such patients will be those who show either a level of apolipoproteins sufficiently high in their blood or plasma such that the artisan will expect in vivo formation of particles such as those described herein, where native apolipoprotein combines with the administered lipid to form the particles which remove the LPS, or those who are hyperlipidemic and thus do require only the peptide to form the requisite construct.

Both the treatment and prophylactic therapies described herein may be carried out in this way.

It is preferred that the peptides of the invention be amphipathic, such that when placed in polar solutions the peptides take on a configuration wherein hydrophobic amino acids cluster preferentially on one face and hydrophilic amino acids cluster on the other. Various three-dimensional structures may result, one of which is the helical wheel configuration of the peptides presented in FIG. 4, which are described in Anantharamariah supra, the disclosure of which is incorporated by reference. Peptide 18A is an especially preferred peptide for use in accordance with the invention.

The lipid to be used in any of the forms of therapy described herein may vary, with phospholipids, and especially phosphatidylcholine being preferred. There are a large number of different endotoxins known to the skilled artisan, and it is only necessary that the lipid be one with which the endotoxin may associate.

The foregoing disclosure sets forth one methodology for preparing the particles of the invention, but other methodologies are equally applicable. For example, one may dissolve the lipid of interest in a solvent, such as sodium cholate/sterile intravenous saline, followed by mixing with the peptide of interest. Cholate is then removed and recombinant particles are prepared in accordance with, e.g. Bonomo et al, J. Lipid. Res 29: 380-384 (1988).

Peptides may be prepared in any of the standard methodologies known to the skilled artisan, including solid phase synthesis, as well as proteolytic cleavage followed by purification, and so forth. The first stated methodology is preferred, in view of the control it affords to the investigator.

The skilled artisan will be aware of various peptides, lipids and endotoxins useful in the invention as described therein, and all are encompassed by applicants' invention.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. Method for alleviating endotoxin caused toxicity in a subject comprising administering to a subject in need thereof an amount of (i) a peptide consisting of the amino acid sequence set forth in SEQ ID NO; 1 and (ii) a phosphatidylcholine, wherein (i) and (ii) are present in the form of an HDL like particle with which said endotoxin associates, in an amount sufficient to alleviate said toxicity.

2. Method of claim 1, wherein said endotoxin is an *E. coli* endotoxin.

3. Method of claim 1, wherein said endotoxin is an *S. tymphimurium* endotoxin.

4. Method for alleviating endotoxin caused toxicity in a subject comprising administering to a subject in need thereof, separate and consecutive administrations of (i) a peptide consisting of the amino acid sequence f SEQ ID NO: 1 and (ii) a phosphatidylcholine with which said endotoxin associates, wherein (i) and (ii) are administered in an amount of each sufficient to alleviate said toxicity.

5. Method of claim 4, wherein said endotoxin is an *E. coli* endotoxin.

6. Method of claim 4, wherein said endotoxin is an *S. typhimurium* endotoxin.

7. Method for reducing risk of endotoxin caused toxicity in a subject comprising administering to a subject who is to be subjected to exposure to an endotoxin an amount of (i) a peptide consisting of the amino acid sequence set forth in SEQ ID NO 1 and (ii) a phosphatidylcholine with which said endotoxin associates, wherein (i) and (ii) are present in the form of an HDL like particle, in an amount sufficient to reduce risk of endotoxin caused toxicity.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO: 1:

```
Asp  Trp  Leu  Lys  Ala  Phe  Tyr  Asp  Lys  Val  Ala  Glu  Lys  Leu  Lys
 5                        10                        15
Glu  Ala  Phe
```

( 2 ) INFORMATION FOR SEQ ID NO: 2:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO: 2:

```
Lys  Trp  Leu  Asp  Ala  Phe  Tyr  Lys  Asp  Val  Ala  Lys  Glu  Leu  Glu  Lys
 5                        10                        15
Ala  Phe
```

( 2 ) INFORMATION FOR SEQ ID NO: 3:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO: 3:

```
Asp  Trp  Leu  Lys  Ala  Phe  Tyr  Asp  Lys  Ala  Glu  Lys  Leu  Lys  Glu  Ala
 5                        10                        15
Phe
```

( 2 ) INFORMATION FOR SEQ ID NO: 4:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 4:

```
Pro  Lys  Leu  Glu  Glu  Leu  Lys  Glu  Lys  Leu  Lys  Glu  Leu  Leu  Glu  Lys
 5                        10                        15
Leu  Lys  Glu  Lys  Leu  Ala
20
```

( 2 ) INFORMATION FOR SEQ ID NO: 5:

( i ) SEQUENCE CHARACTERISTICS:

(A) LENGTH: 16 amino acids
(B) TYPE: amino acid
(D) TOPOLOGY: linear (xi) SEQUENCE DESCRIPTION: SEQ ID NO: 5:

Val Ser Ser Leu Lys Glu Tyr Trp Ser Ser Leu Lys Glu Ser Phe Ser
 5                   10                  15

(2) INFORMATION FOR SEQ ID NO: 6:

(i) SEQUENCE CHARACTERISTICS:
    (A) LENGTH: 20 amino acids
    (B) TYPE: amino acid
    (D) TOPOLOGY: linear (xi) SEQUENCE DESCRIPTION: SEQ ID NO: 6:

Val Ser Ser Leu Leu Ser Ser Leu Lys Glu Tyr Trp Ser Ser Leu Lys
 5                   10                  15

Glu Ser Leu Ser
 20

(2) INFORMATION FOR SEQ ID NO: 7:

(i) SEQUENCE CHARACTERISTICS:
    (A) LENGTH: 24 amino acids
    (B) TYPE: amino acid
    (D) TOPOLOGY: linear (xi) SEQUENCE DESCRIPTION: SEQ ID NO: 7:

Val Ser Ser Leu Leu Ser Ser Leu Leu Ser Ser Leu Lys Glu Tyr Trp
 5                   10                  15

Ser Ser Leu Lys Glu Ser Glu Ser
 20

(2) INFORMATION FOR SEQ ID NO: 8:

(i) SEQUENCE CHARACTERISTICS:
    (A) LENGTH: 22 amino acids
    (B) TYPE: amino acid
    (D) TOPOLOGY: linear (xi) SEQUENCE DESCRIPTION: SEQ ID NO: 8:

Pro Val Leu Asp Glu Phe Arg Glu Lys Leu Asn Glu Glu Leu Glu Ala
 5                   10                  15

Leu Lys Gln Lys Met Lys
 20

(2) INFORMATION FOR SEQ ID NO: 9:

(i) SEQUENCE CHARACTERISTICS:
    (A) LENGTH: 22 amino acids
    (B) TYPE: amino acid
    (D) TOPOLOGY: linear (xi) SEQUENCE DESCRIPTION: SEQ ID NO: 9:

Pro Leu Ala Glu Asp Leu Gln Thr Lys Leu Asn Glu Asn Val Glu Asp
 5                   10                  15

Leu Arg Lys Gln Leu Val
 20